United States Patent [19]

Hayes

[11] 3,979,277

[45] Sept. 7, 1976

[54] HYDROPROCESSING OF HYDROCARBONS

[75] Inventor: John C. Hayes, Palatine, Ill.

[73] Assignee: Universal Oil Products Company, Des Plaines, Ill.

[22] Filed: Feb. 21, 1975

[21] Appl. No.: 551,955

Related U.S. Application Data

[60] Division of Ser. No. 443,046, Feb. 15, 1974, Pat. No. 3,900,386, which is a continuation-in-part of Ser. No. 365,782, May 31, 1973, Pat. No. 3,839,193, which is a continuation-in-part of Ser. No. 27,457, April 10, 1970, abandoned.

[52] U.S. Cl. ............................... 208/143; 208/255; 260/677 H
[51] Int. Cl.$^2$ ........................................ C10G 23/04
[58] Field of Search ........................... 208/143, 255; 260/677 H; 252/466 PT

[56] References Cited
UNITED STATES PATENTS

| | | | |
|---|---|---|---|
| 2,848,377 | 8/1958 | Webb | 252/466 PT |
| 3,607,728 | 9/1971 | Wilhelm | 208/255 |
| 3,642,660 | 2/1972 | Mitsche | 252/466 PT |

Primary Examiner—Herbert Levine
Attorney, Agent, or Firm—James R. Hoatson, Jr.; Thomas K. McBride; William H. Page, II

[57] ABSTRACT

A process for hydrotreating (hydroprocessing) hydrocarbons and mixtures of hydrocarbons utilizing a catalytic composite of a porous carrier material, a platinum or palladium component, an iridium component and a germanium component, in which process there is effected a chemical consumption of hydrogen. A specific example of one such catalyst is a composite of a crystalline aluminosilicate, a platinum component, an iridium component and a germanium component, for utilization in a hydrocracking process. Other hydrocarbon hydroprocesses are directed toward the hydrogenation of aromatic nuclei, the ring-opening of cyclic hydrocarbons, desulfurization, denitrification, hydrogenation, etc.

4 Claims, No Drawings

HYDROPROCESSING OF HYDROCARBONS

RELATED APPLICATIONS

The present application is a division of my copending application, Ser. No. 443,046 filed Feb. 15, 1974, now U.S. Pat. No. 3,900,386, which is a Continuation-in-Part of my application, Ser. No. 365,782, now U.S. Pat. No. 3,839,193, filed May 31, 1973, which, in turn, is a Continuation-in-Part of my application, Ser. No. 27,457 filed Apr. 10, 1970, now abandoned, all the teachings of these applications are incorporated herein by specific reference thereto.

APPLICABILITY OF INVENTION

The present invention encompasses the use of a catalytic composite of a porous carrier material, a platinum or palladium component, an iridium component and a germanium component in the hydrotreating of hydrocarbons and mixtures of hydrocarbons. As utilized herein, the term "hydrotreating" is intended to be synonymous with the term "hydroprocessing", which involves the conversion of hydrocarbons at operating conditions selected to effect a chemical consumption of hydrogen. Included within the processes intended to be encompassed by the term hydroprocessing are hydrocracking, aromatic hydrogenation, ring-opening, hydrorefining (for nitrogen removal and olefin saturation), desulfurization (often included in hydrorefining) and hydrogenation, etc. As will be recognized, one common attribute of these processes, and the reactions being effected therein, is that they are all "hydrogen-consuming", and are, therefore, exothermic in nature.

The individual characteristics of the foregoing hydrotreating processes, including preferred operating conditions and techniques, will be herinafter described in greater detail. The subject of the present invention is the use of a catalytic composite which has exceptional activity and resistance to deactivation when employed in a hydrogen-consuming process. Such processes require a catalyst having both a hydrogenation function and a cracking function. More specifically, the present process uses a dual-function catalytic composite which enables substantial improvements in those hydroprocesses that have traditionally used a dual-function catalyst. The particular catalytic composite constitutes a porous carrier material, a platinum or palladium component, an iridium component and a germanium component; specifically, an improved hydrocracking process utilizes a crystalline aluminosilicate carrier material, a platinum component, an iridium component and a germanium component for improved activity, product selectivity and operational stability characteristics.

Composites having dual-function catalytic activity are widely employed in many industries for the purpose of accelerating a wide spectrum of hydrocarbon conversion reactions. Generally, the cracking function is thought to be associated with an acidacting material of the porous, adsorptive refractory inorganic oxide type which is typically utilized as the carrier material for a metallic component from the metals, or compounds of metals, of Groups V through VIII of the Periodic Table, to which the hydrogenation function is generally attributed.

Catalytic composites are used to promote a wide variety of hydrocarbon conversion reactions such as hydrocracking, isomerization, dehydrogenation, hydrogenation, desulfurization, reforming, ring-opening, cyclization, aromatization, alkylation and transalkylation, polymerization, cracking etc., some of which reactions are hydrogen-producing while others are hydrogen-consuming. In using the term "hydrogen-consuming", I intend to exclude those processes wherein the only hydrogen consumption involves the saturation of light olefins, resulting from undesirable cracking, which produces the light paraffins, methane, ethane and propane. It is to the latter group of reactions, hydrogen-consuming, that the present invention is applicable. In many instances, the commercial application of these catalysts is in processes where more than one of these reactions proceed simultaneously. An example of this type of process is a hydrocracking process wherein catalysts are utilized to effect selective hydrogenation and cracking of high molecular weight materials to produce a lower-boiling, more valuable output stream. Another such example would be the conversion of aromatic hydrocarbons into jet fuel components, principally straight, or slightly branched paraffins.

Regardless of the reaction involved, or the particular process, it is very important that the catalyst exhibit not only the capability to perform its specified functions initially, but also perform them satisfactorily for prolonged periods of time. The analytical terms employed in the art to measure how efficient a particular catalyst performs its intended functions in a particular hydrocarbon conversion process, are activity, selectivity and stability. For the purpose of discussion, these terms are conveniently defined herein for a given charge stock, as follows: (1) activity is a measure of the ability of the catalyst to convert a hydrocarbon feed stock into products at a specified severity level, where severity level alludes to the operating conditions employed—the temperature, pressure, liquid hourly space velocity and hydrogen concentration; (2) selectivity refers to the weight percent or volume percent of the reactants that are converted into the desired product and/or products; (3) stability connotes the rate of change of the activity and selectivity parameters with time—obviously, the smaller rate implying the more stable catalyst. With respect to a hydrogen-consuming process, for example hydrocracking, activity, stability and selectivity are similarly defined. Thus, "activity" connotes the quantity of charge stock, boiling above a given temperature, which is converted to hydrocarbons boiling below the given temperature. "Selectivity" refers to the quantity of converted charge stock which boils below the desired end point of the product, as well as above a minimum specified initial boiling point. "Stability" connotes the rate of change of activity and selectivity. Thus, for example, where a gas oil, boiling above about 650°F., is subjected to hydrocracking, activity connotes the conversion of 650°F.-plus charge stock to 650°F.-minus product. Selectivity can allude to the quantity of conversion into gasoline boiling range hydrocarbons--i.e., pentanes and heavier, normally liquid hydrocarbons boiling up to about 400°F. Stability might be conveniently expressed in terms of temperature increase required during various increments of catalyst life, in order to maintain the desired activity.

As is well known to those skilled in the art, the principal cause of observed deactivation or instability of a dual-function catalyst is associated with the fact that coke forms on the surface of the catalyst during the course of the reaction. More specifically, in the various hydrocarbon conversion processes, and especially those which are categorized as hydrogen-consuming, the operating conditions utilized result in the formation of high molecular weight, black, solid or semi-solid, hydrogen-poor carbonaceous material which coats the surface of the catalyst and reduces its activity by shielding its active sites from the reactants. Accordingly, a major problem facing workers in this area in the development of more active and selective catalytic composites that are not as sensitive to the presence of these carbonaceous materials and/or have the capability to suppress the rate of formation of these materials at the operating conditions employed in a particular process.

I have now found a dual-function catalytic composite which processes improved activity, selectivity and stability when employed in the hydroprocessing of hydrocarbons, wherein there is effected a chemical consumption of hydrogen. In particular, I have found that the use of a catalytic composite of a platinum or palladium component, an iridium component and a germanium component with a porous carrier material improves the overall operation of these hydrogen-consuming processes. However, I have determined that a catalytic composite of a crystalline aluminosilicate carrier material, a platinum component, an iridium component and a germanium component, when utilized in a process for hydrocracking hydrocarbonaceous material into lower-boiling hydrocarbon products, affords substantial improvement in performance and results. As indicated, the present invention essentially involves the use of a catalyst in which a germanium component and an iridium component has been added to a dual-function conversion catalyst, and enables the performance characteristics of the process to be sharply and materially improved.

An essential condition associated with the acquisition of this improved performance is the oxidation state of the germanium component utilized in this catalyst. As a result of my investigations, I have determined that the germanium component must be utilized in a positive oxidation state (i.e., either +2 or +4) and that the germanium component must be uniformly distributed throughout the porous carrier material. Furthermore, the catalyst must be prepared under carefully controlled conditions as will be explained hereinafter. In the case of a hydrocracking process, one of the principal advantages associated with the use of the novel catalyst of the present invention involves the acquisition of the capability to operate in a stable manner in a high severity operation. In short, the present invention essentially involves the finding that the addition of a controlled amount of a germanium component, in a positive oxidation state, to a dual-function hydrocarbon conversion catalyst containing a platinum or palladium component enables performance characteristics of the catalyst to be sharply and materially improved when used in a hydrogen-consuming process.

OBJECTS AND EMBODIMENTS

An object of the present invention is to afford a process for the hydroprocessing of a hydrocarbon, or mixture of hydrocarbons. A corollary objective is to improve the selectivity and stability of hydroprocessing utilizing a highly active, germanium component-containing and iridium component-containing catalytic composite.

A specific object of my invention in the improvement of hydrogen-consuming processes including hydrocracking, hydrorefining, ring-opening for jet fuel production, hydrogenation of aromatic hydrocarbons, desulfurization, denitrification, etc. Therefore, in one embodiment, the present invention encompasses a hydrocarbon hydroprocess which comprises reacting a hydrocarbon with hydrogen at conditions selected to effect chemical consumption of hydrogen and in contact with a catalytic composite of a platinum or palladium component, an iridium component, a germanium component and a porous carrier material. In another embodiment, the operating conditions include a pressure of from 400 to about 5,000 psig., an LHSV (defined as volumes of liquid hydrocarbon change per hour per volume of catalyst disposed in the reaction zone) of from 0.1 to about 10.0, a hydrogen circulation rate of from 1,000 to about 50,000 scf./Bbl. and a maximum catalyst temperature of from 200°F. to about 900°F.

In another embodiment, the process is further characterized in that the catalytic composite is reduced and sulfided prior to contacting the hydrocarbon feed stream. In still another embodiment, my invention involves a process for hydrogenating a coke-forming hydrocarbon distillate containing di-olefinic and mono-olefinic hydrocarbons, and aromatics, which process comprises reacting said distillate with hydrogen, at a temperature below about 500°F., in contact with a catalytic composite of an alumina-containing refractory inorganic oxide, a platinum or palladium component, an alkali metal component, an iridium component and a germanium component, and recovering an aromatic/mono-olefinic hydrocarbon concentrate substantially free from conjugated di-olefinic hydrocarbons.

Another embodiment affords a catalytic composite comprising a substantially pure crystalline aluminosilicate material, at least about 90.0% by weight of which is zeolitic, a platinum or palladium component, an iridium component and a germanium component.

Other objects and embodiments of my invention relate to additional details regarding preferred catalytic ingredients, the concentration of components in the catalytic composite, methods of catalyst preparation, individual operating conditions for use in the various hydrotreating processes, preferred processing techniques and the like particulars which are hereinafter given in the following, more detailed summary of my invention.

SUMMARY OF THE INVENTION

As hereinabove set forth, the present invention involves the hydroprocessing of hydrocarbons and mixtures of hydrocarbons, utilizing a particular catalytic composite. This catalyst comprises a porous carrier material having combined therewith a platinum or palladium component, an iridium component and a germanium component; in many applications, the catalytic composite will also contain a halogen component, and in some select applications, an alkali metal or alkaline-earth metal component. Considering first the porous carrier material, it is preferred that it be a porous, adsorptive, high-surface area support having a surface area of about 25 to about 500 square meters per gram. The porous carrier material is necessarily relatively refractory with respect to the operating conditions employed in the particular hydrotreating process, and it is intended to include carrier materials which have traditionally been utilized in dual-function hydrocarbon conversion catalysts. In particular, suitable carrier materials are selected from the group of amorphous refractory inorganic oxides including alumina, titania, zirconia, chromia, magnesia, thoria, boria, silica-alumina, silica-magnesia, chromia-alumina, alumina-boria, alumina-silica-boron phosphate, silica-zirconia, etc. When of the amorphous type, the preferred carrier material is a composite of alumina and silica with silica being present in an amount of about 10.0% to about 90.0% by weight.

In many hydroprocessing applications of the present invention, particularly hydrocracking heavy hydrocarbonaceous material to produce lower-boiling hydrocarbon products, the carrier material will constitute a crystalline aluminosilicate, often referred to as being zeolitic in nature. This may be naturally-occurring, or synthetically prepared, and includes mordenite, faujasite, Type A or Type U molecular sieves, etc. When utilized as the carrier material, the zeolitic material may be in the hydrogen form, or in a form which has been treated with multi-valent cations.

As hereinabove set forth, the porous carrier material, for use in the process of the present invention, is a refractory inorganic oxide, either alumina in and of itself, or in combination with one or more other refractory inorganic oxides, and particularly in combination with silica. When utilized as the sole component of the carrier material, the alumina may be of the gamma-, eta, or theta-alumina type, with gamma-, or eta-alumina giving the best results. In addition, the preferred carrier materials have an apparent bulk density of about 0.30 to about 0.70 gm./cc. and surface area characteristics such that the average pore diameter is about 20 to about 300 Angstroms, the pore volume is about 0.10 to about 1.0 milliliters per gram and the surface area is about 100 to about 500 square meters per gram. Whatever type of refractory inorganic oxide is employed, it may be activated prior to use by one or more treatments including drying, calcination steaming, etc. For example, the alumina carrier may be prepared by adding a suitable alkaline reagent, such as ammonium hydroxide, to a salt of aluminum, such as aluminum chloride, aluminum nitrate, etc., in an amount to form an aluminum hydroxide gel which, upon drying and calcination, is converted to alumina. The carrier material may be formed in any desired shape such as spheres, pills, cakes extrudates, powders, granules, etc., and may further be utilized in any desired size.

When a crystalline aluminosilicate, or zeolitic material, is intended for use as the carrier, it may be prepared in a number of ways. One common way is to mix solutions of sodium silicate, or colloidal silica, and sodium aluminate, and allow these solutions to react to form a solid crystalline aluminosilicate. Another method is to contact a solid inorganic oxide, from the group of silica, alumina, and mixtures thereof, with an aqueous treating solution containing alkali metal cations (preferably sodium) and anions selected from the group of hydroxyl, silicate and aluminate, and allow the solid-liquid mixture to react until the desired crystalline aluminosilicate has been formed. One particular method is especially preferred when the carrier material is intended to be a crystalline aluminosilicate. This stems from the fact that the method can produce a carrier material of sustantially pure crystalline aluminosilicate particles. In employing the term "substantially pure", the intended connotation is an aggregate particle at least 90.0% by weight of which is zeolitic. Thus, this carrier is distinguished from an amorphous carrier material, or prior art pills and/or extrudes in which the zeolitic material might be dispersed within an amorphous matrix with the result that only about 40.0% to about 70.0% by weight of the final particle is zeolitic. The preferred method of preparing the carrier material produces crystalline aluminosilicates of the faujasite modification, and utilizes aqueous solutions of colloidal silica and sodium aluminate. Colloidal silica is a suspension in which the suspended particles are present in very finely divided form—i.e., having a particle size from about 1 to about 500 millimicrons in diameter. The type of crystalline aluminosilicate which is produced is primarily dependent upon the conditions under which crystallization occurs, with the $SiO_2/Al_2O_3$ ratio, the $Na_2O/SiO_2$ ratio, the $H_2O/Na_2O$ ratio, temperature and time being the important variables.

After the solid crystalline aluminosilicate has been formed, the motor liquid is separated from the solids by methods such as decantation or filtration. The solids are water-washed and filtered to remove undesirable ions, and to reduce the quantity of amorphous material, and are then reslurried in water to a solids concentration of about 5.0% to about 50.0%. The cake and the water are violently agitated and homogenized until the agglomerates are broken and the solids are uniformly dispersed in what appears to be a colloidal suspension. The suspension is then spray dried by conventional means such as pressuring and suspension through an orific into a hot, dry chamber. The solid particles are withdrawn from the drying chamber and are suitable for forming into finished particles of desired size and shape. The preferred form of the finished particles is a cylindrical pill, and these may be prepared by introducing the spray-dried particles directly into a pilling machine without the addition of any extraneous lubricant or binder. The pilling machines are adjusted to produce particles having a crushing strength of from 2 to 20 pounds, and preferably from 5 to 15 pounds. The pilled faujasite carrier material, of which at least about 90.0% by weight is zeolitic, is activated catalytically by converting the sodium form either to the divalent ion form, the hydrogen form or mixtures thereof.

One essential constituent of the composite of the present invention is a germanium component, and it is an essential feature of the catalyst used in hydroprocessing according to the present invention, that the germanium component is present in the composite in an oxidation state above that of the elemental metal. That is to say, the germanium component necessarily exists within the catalytic composite in either the +2 or +4 oxidation state, the latter being the most likely state. Accordingly, the germanium component will be presend in the composite as a chemical compound, such as the oxide, sulfide, halide, etc., wherein the germanium is in the required oxidation state, or as a chemical combination with the carrier material in which combination the germanium exists in this higher oxidation state. On the basis of the evidence currently available, it is believed that the germanium component in the subject composite exists as germanous or germanic oxide. It is important to note that this limitation on the state of the germanium component requires extreme care in the preparation and use of the subject composite in order to insure that it is not subjected to high temperature reduction conditions (reduction at temperatures above 1000°F.) effective to produce the germanium metal. This germanium component may be incorporated in the catalytic composite in any suitable manner known to the art such as by co-precipitation or cogellation with the porous carrier material, ion-exchange with the gelled carrier material or impregnation with the carrier material either after or before it is dried and calcined. It is to be noted that it is intended to include within the scope of the present invention all conventional methods for incorporating a metallic component in a catalytic composite and the particular method of incorporation used is not deemed to be an essential feature of the present invention. One method of incorporating the germanium component into the catalytic composite involves co-precipitating the germanium component during the preparation of the carrier material. This method typically involves the addition of a suitable soluble germanium material such as germanium tetrachloride to the inorganic oxide hydrosol and then combining the hydrosol with a suitable gelling agent and dropping the resultant mixture into an oil bath maintained at elevated temperatures. The droplets remain in the oil bath until they set and form hydrogel spheres. The spheres are withdrawn from the oil bath and subjected to specific aging treatments in oil and in an ammoniacal solution. The aged spheres are washed and dried at a temperature of about 200°F. to 400°F., and thereafter calcined at an elevated temperature of about 850°F. to about 1300°F. Further details of spherical particle production may be found in U.S. Pat. No. 2,620,341, issued to James Hoekstra. After drying and calcining the resulting gelled carrier material there is obtained an intimate combination of alumina and germanium oxide. A preferred method of incorporating the germanium component into the catalytic composite involves utilization of a soluble, decomposable compound of germanium to impregnate the porous carrier material. In general, the solvent used in this impregnation step is selected on the basis of the capability to dissolve the desired germanium compound and is preferably an aqueous, or alcoholic solution. Thus, the germanium component may be added to the carrier material by commingling the latter with a solution of a suitable germanium salt or suitable compound of germanium such as germanium tetrachloride, germanium difluoride, germanium tetrafluoride, germanium diiodide, germanium monosulfide, and the like compounds. In general, the germanium component can be impregnated either prior to, simultaneously with, or after the other metallic components are added to the carrier material. However, I have found that excellent results are obtained when the germanium component is impregnated simultaneously with the other metallic components. In fact, I have determined that a preferred impregnation solution contains chloroplatinic acid, hydrogen chloride, chloroiridic acid, and germanous oxide dissolved in chlorine water, especially when the catalyst is intended to contain combined chlorine. I have also determined that another impregnation solution comprises chloroplatinic acid, hydrogen chloride, chloroiridic acid and germanium tetrachloride dissolved in ethanol. Best results are believed to be obtained when this component exists in the composite as germanium oxide. Following the impregnation step, the resulting composite is dried and calcined as explained hereinafter.

Regardless of which germanium compound is used in the preferred impregnation step, it is important that the germanium component be uniformly distributed throughout the carrier material. It is preferred to use a volume ratio of impregnation solution to carrier material of at least 1.5:1 and preferably about 2:1 to about 10:1 or more. Similarly, it is preferred to use a relatively long contact time during the impregnation step ranging from about one-fourth hour up to about one-half hour or more before drying to remove excess solvent in order to insure a high dispersion of the germanium component on the carrier material. The carrier material is, likewise, preferably constantly agitated during this preferred impregnation step.

As previously indicated, the catalyst for use in the process of the present invention also contains a platinum or palladium component. Although the process of the present invention is specifically directed to the use of a catalytic composite containing platinum, it is intended to include palladium. The platinum or palladium component, for example platinum, may exist within the final catalytic composite as a compound such as an oxide, sulfide, halide, etc., or in an elemental state. The platinum or palladium component generally comprises about 0.01% to about 2.0% by weight of the final composite, calculated on an elemental basis. Excellent results are obtained when the catalyst contains about 0.3% to about 0.9% by weight of platinum or palladium.

The platinum or palladium component may be incorporated within the catalytic composite in any suitable manner including co-precipitation or cogellation with the carrier material, ion-exchange or impregnation. A preferred method of preparation involves the utilization of a water-soluble compound of platinum or palladium in an impregnation technique. Thus, a platinum component may be added to the carrier material by commingling the latter with an aqueous solution of chloroplatinic acid. Other water-soluble compounds of platinum may be employed, and include ammonium chloroplatinate, platinum chloride, dinitro diamino platinum, etc. The use of a platinum chloride compound, such as chloroplatinic acid, is preferred since it facilitates the incorporation of both the platinum component and at least a minor quantity of the halogen component in a single step. In addition, it is generally preferred to impregnate the carrier material after it has been calcined in order to minimize the risk of washing away the valuable platinum or palladium metal compounds, however, in some instances it may prove advantageous to impregnate the carrier material when it exists in a gelled state. Following impregnation, the composite will generally be dried at a temperature of about 200°F. to about 400°F., for a period of from 2 to about 24 hours, or more, and finally calcined at a temperature of about 700°F. to 1100°F., in an atmosphere of air, for a period of about 0.5 to about 10 hours.

Yet another essential ingredient of the present catalytic composite is an iridium component. It is of fundamental importance that substantially all the iridium component exists within the catalytic composite of the present invention in the elemental state and the subsequently described reduction procedure is designed to accomplish this objective. The iridium component may be utilized in the composite in any amount which is catalytically effective, with the preferred amount being about 0.01 to about 2 wt. % thereof, calculated on an elemental iridium basis. Typically best results are obtained with about 0.05 to about 1 wt. % iridium. It is, additionally, preferred to select the specific amount of iridium from within this broad weight range as a function of the amount of the platinum or palladium component, on an atomic basis, as is explained hereinafter.

This iridium component may be incorporated into the catalytic composite in any suitable manner known to those skilled in the catalyst formulation art which results in a relatively uniform dispersion of iridium in the carrier material. In addition, it may be added at any stage of the preparation of the composite—either during preparation of the carrier material or thereafter——and the precise method of incorporation used is not deemed to be critical. However, best results are thought to be obtained when the iridium component is relatively uniformly distributed throughout the carrier material, and the preferred procedures are the ones known to result in a composite having this relatively uniform distribution. One acceptable procedure for incorporating this component into the composite involves cogelling or coprecipitating the iridium component during the preparation of the carrier material. A preferred way of incorporating this component is an impregnation step wherein the porous carrier material is impregnated with a suitable iridium-containing solution either before, during or after the carrier material is calcined. Preferred impregnation solutions are aqueous solutions of water soluble, decomposable iridium compounds such as iridium tribromide, iridium dichloride, iridium tetrachloride, iridium oxalic acid, iridium sulfate, potassium iridochloride, chloroiridic acid and the like compounds. Best results are ordinarily obtained when the impregnation solution is an aqueous solution of chloroiridic acid or sodium chloroiridate. This component can be added to the carrier material, either prior to, simultaneously with or after the other metallic components are combined therewith. Best results are usually achieved when this component is added simultaneously with the other metallic components. In fact, excellent results are obtained, as reported in the examples, with a one step impregnation procedure using an aqueous solution comprising chloroplatinic or chloropalladic acid, chloroiridic acid, hydrochloric acid and germanium tetrachloride dissolved in anhydrous alcohol.

Although not essential to successful hydroprocessing in all cases, in fact detrimental in some, a halogen component may be incorporated into the catalytic composite. Accordingly, a preferred catalytic composite, for use in the present process, comprises a combination of a platinum or palladium component, a germanium component, an iridium component and a halogen component. Although the precise form of the chemistry of the association of the halogen component with the carrier material and metallic components is not accurately known, it is customary in the art to refer to the halogen component as being combined with the carrier material, or with the other ingredients of the catalyst. The combined halogen may be either fluorine, chlorine, iodine, bromine, or mixtures thereof. Of these fluoride and particularly chlorine are preferred for the hydrocarbon hydroprocesses encompassed by the present invention. The halogen may be added to the carrier material in any suitable manner, and either during preparation of the carrier or before, or after the addition of the other components. For example, the halogen may be added at any stage of the preparation of the carrier material, or to the calcined carrier material, as an aqueous solution of an acid such as hydrogen fluoride, hydrogen chloride, hydrogen bromide, hydrogen iodide, etc. The halogen component or a portion thereof may be composited with the carrier material during the impregnation of the latter with the metal components. The inorganic oxide hydrosol, which is typically utilized to form an amorphous carrier material, may contain halogen and thus contribute at least a portion of the halogen component to the final composite. The quantity of halogen is such that the final catalytic composite contains about 0.1% to about 1.5% by weight, and preferably from about 0.5% to about 1.2%, calculated on an elemental basis.

Regarding the preferred amounts of the various metallic components of the subject catalyst, I have found it to be good practice to specify the amounts of the iridium component and the germanium component as a function of the amount of the platinum or palladium component. On this basis, the amount of the iridium component is ordinarily selected so that the atomic ratio or iridium to platinum or palladium metal contained in the composite is about 0.1:1 to about 2:1, with the preferred range being about 0.25:1 to about 1.5:1. Similarly, the amount of the germanium component is ordinarily selected to produce a composite containing an atomic ratio of germanium to platinum or palladium metal of about 0.3:1 to about 10:1, with the preferred range being about 0.6:1 to about 6:1.

Another significant parameter for the instant catalyst is the "total metals content" which is defined to be the sum of the platinum or palladium component, the iridium component and the germanium component, calculated on an elemental metal basis. Good results are ordinarily obtained with the subject catalyst when this parameter is fixed at a value of about 0.15 to about 3 wt. %, with best results ordinarily achieved at a metals loading of about 0.3 to about 2 wt. %.

In embodiments of the present invention wherein the instant trimetallic catalytic composite is used for the hydrogenation of hydrogenatable hydrocarbons, it is ordinarily a preferred practice to include an alkali or alkaline earth metal component in the composite. More precisely, this optional component is selected from the group consisting of the compounds of the alkali metals — cesium, rubidium, potassium, sodium, and lithium — and the compounds of the alkaline earth metals — calcium, strontium, barium and magnesium. Generally, good results are obtained in these embodiments when this component constitutes about 1 to about 5 wt. % of the composite, calculated on an elemental basis. This optional alkali or alkaline earth metal component can be incorporated in the composite in any of the known ways, with impregnation with an aqueous solution of a suitable water-soluble, decomposable compound being preferred.

An optional ingredient for the trimetallic catalyst of the present invention is a Friedel-Crafts metal halide component. This ingredient is particularly useful in hydrocarbon conversion embodiments of the present invention wherein it is preferred that the catalyst utilized has a strong acid or cracking function associated therewith — for example, an embodiment wherein hydrocarbons are to be hydrocracked or isomerized with the catalyst of the present invention. Suitable metal halides of the Friedel-Crafts type include aluminum chloride, aluminum bromide, ferric chloride, ferric bromide, zinc chloride and the like compounds, with the aluminum halides and particularly aluminum chloride ordinarily yielding best results. Generally, this optional ingredient can be incorporated into the composite of the present invention by way of the conventional methods for adding metallic halides of this type; however, best results are ordinarily obtained when the metallic halide is sublimed onto the surface of the carrier material according to the preferred method disclosed in U.S. Pat. No. 2,999,074. The component can generally be utilized in any amount which is catalytically effective, with a value selected from the range of about 1 to about 100 wt. % of the carrier material generally being preferred. When used in many of the hydrogen-consuming processes hereinbefore described, the foregoing quantities of metallic components will be combined with a carrier material of alumina and silica, wherein the silica concentration is 10.0% to about 90.0% by weight.

Regardless of the details of how the components of the catalyst are combined with the porous carrier material, the final catalyst generally will be dried at a temperature of about 200° to about 600°F. for a period of at least about 2 to about 24 hours or more, and finally calcined or oxidized at a temperature of about 700°F. to about 1100°F. in an air atmosphere for a period of about 0.5 to about 10 hours in order to convert substantially all of the metallic components substantially to the oxide form. Because a halogen component may be utilized in the catalyst, best results are generally obtained when the halogen content of the catalyst is adjusted during the calcination step by including a halogen or a halogen-containing compound in the air atmosphere utilized. In particular, when the halogen component of the catalyst is chlorine, it is preferred to use a mole ratio of $H_2O$ to HCl of about 5:1 to about 100:1 during at least a portion of the calcination step in order to adjust the final chlorine content of the catalyst to a range of about 0.5 to about 1.5 wt. %.

It is an essential feature of the present invention that the resultant oxidized catalytic composite is subjected to a substantially water-free reduction step prior to its use in the conversion of hydrocarbons. This step is designed to selectively reduce the platinum or palladium and iridium components to the corresponding metals and to insure a uniform and finely divided dispersion of these metallic components throughout the carrier material, while maintaining the germanium component in a positive oxidation state. Preferably, substantially pure and dry hydrogen (i.e., less than 20 vol. ppm. $H_2O$) is used as the reducing agent in this step. The reducing agent is contacted with the oxidized catalyst at conditions including a temperature of about 800°F. to about 1200°F. and a period of time of about 0.5 to 2 hours effective to reduce substantially all of the platinum or palladium and iridium components to their elemental metallic state while maintaining the germanium component in an oxidation state above that of the elemental metal. This reduction treatment may be performed in situ as part of a start-up sequence if precautions are taken to predry the plant to a substantially water-free state and if substantially water-free hydrogen is used.

The resulting reduced catalytic composite may, in some cases, be beneficially subjected to a presulfiding operation designed to incorporate in the catalytic composite from about 0.05 to about 0.5 wt. % sulfur calculated on an elemental basis. Preferably, this presulfiding treatment takes place in the presence of hydrogen and a suitable sulfur-containing compound such as hydrogen sulfide, lower molecular weight mercaptans, organic sulfides, etc. Typically, this procedure comprises treating the selectively reduced catalyst with a sulfiding gas such as a mixture of hydrogen and hydrogen sulfide having about 10 moles of hydrogen per mole of hydrogen sulfide at conditions sufficient to effect the desired incorporation of sulfur, generally including a temperature ranging from about 50°F. up to about 1100°F. or more. It is generally a good practice to perform this presulfiding step under substantially water-free conditions.

According to the present invention, a hydrocarbon charge stock and hydrogen are contacted with a trimetallic catalyst of the type described above in a hydrocarbon conversion zone. This contacting may be accomplished by using the catalyst in a fixed bed system, a moving bed system, a fluidized bed system, or in a batch type operation; however, in view of the danger of attrition losses of the valuable catalyst and of well known operational advantages, it is preferred to use a fixed bed system. In this system, a hydrogen-rich gas and the charge stock are preheated by any suitable heating means to the desired reaction temperature and then are passed, into a conversion zone containing a fixed bed of the catalyst type previously characterized. It is, of course, understood that the conversion zone may be one or more separate reactors with suitable means therebetween to insure that the desired conversion temperature is maintained at the entrance to each reactor. It is also important to note that the reactants may be contacted with the catalyst bed in either upward, downward, or radial flow fashion with the latter being preferred. In addition, the reactants may be in the liquid phase, a mixed liquid-vapor phase, or a vapor phase when they contact the catalyst.

The operating conditions imposed upon the reaction zones are dependent upon the particular hydroprocessing being effected. However, these operating conditions will include a pressure from about 400 to about 5,000 psig., a liquid hourly space velocity of about 0.1 to about 10.0, and a hydrogen circulation rate within the range of about 1,000 to about 50,000 standard cubic feet per barrel. In view of the fact that the reactions being effected are exothermic in nature, an increasing temperature gradient is experienced as the hydrogen and feed stock traverses the catalyst bed. For any given hydrogen-consuming process, it is desirable to maintain the maximum catalyst bed temperature below about 900°F., which temperature is virtually identical to that conveniently measured at the outlet of the reaction zone. Hydrogen-consuming processes are conducted at a temperature in the range of about 200°F. to about 900°F., and it is intended herein that the stated temperature of operation alludes to the maximum catalyst bed temperature. In order to assure that the catalst bed temperature does not exceed the maximum allowed for a given process, the use of conventional quench streams, either normally liquid or gaseous, introduced at one or more intermediate loci of the catalyst bed, may be utilized. In some of the hydrocarbon hydroprocesses encompassed by the present invention, and especially where hydrocracking a heavy hydrocarbonaceous material to produce lower-boiling hydrocarbon products, that portion of the normally liquid product effluent boiling above the end point of the desired product will be recycled to combine with the fresh hydrocarbon charge stock. It these situations, the combined liquid feed ratio (defined as volumes of total liquid charge to the reaction zone per volume of fresh feed charge to the reaction zone) will be within the range of about 1.1 to about 6.0.

Specific operating conditions, processing techniques, particular catalytic composites and other individual process details will be given in the following detailed description of several of the hydrocarbon hydroprocesses to which the present invention is applicable. These will be presented by way of examples given in conjunction with commercially-scaled operating units. In presenting these examples, it is not intended that the invention be limited to the specific illustrations, nor is it intended that a given process be limited to the particular operating conditions, catalytic composite, processing techniques, charge stock, etc. It is understood, therefore, that the present invention is merely illustrated by the specifics hereinafter set forth.

EXAMPLE I

In this example, the present invention is illustrated as applied to the hydrogenation of aromatic hydrocarbons such as benzene, toluene, the various xylenes, naphthalenes, etc., to form the corresponding cyclic paraffins. When applied to the hydrogenation of aromatic hydrocarbons, which are contaminated by sulfurous compounds, primarily thiphenic compounds, the process is advantageous in that it affords 100.0% conversion without the necessity for the substantially complete prior removal of the sulfur compounds. The corresponding cyclic paraffins, resulting from the hydrogenation of the aromatic nuclei, include compounds such as cyclohexane, mono-, di-, tri-substituted cyclohexanes, decahydronaphthalene, tetrahydronaphthalene, etc., which find widespread use as a variety of commercial industries in the manufacture of nylon, as solvents for various fats, oils, waxes, etc.

Aromatic concentrates are obtained by a multiplicity of techniques. For example, a benzene-containing fraction may be subjected to distillation to provide a heart-cut which contains the benzene. This is then subjected to a solvent extraction process which separates the benzene from the normal or iso-paraffinic components, and the naphthenes contained therein. Benzene is readily recovered from the selected solvent by way of distillation, and in a purity of 99.0% or more. Heretofore, the hydrogenation of aromatic hydrocarbons, for example benzene, has been effected with a nickel-containing catalyst. This is extremely disadvantageous in many respects, and especially from the standpoint that nickel is quite sensitive to the minor quantity of sulfurous compounds which may be contained in the benzene concentrate. In accordance with the present process, the benzene is hydrogenated in contact with a non-acidic catalytic composite containing 0.01% to about 2.0% by weight of a platinum or palladium component, from about 0.01% to about 5.0% by weight of a germanium component from about 0.01% to about 2% by weight of an iridium component and from about 0.01% to about 1.5% by weight of an alkalinous metal component. Operating conditions include a maximum catalyst bed temperature in the range of about 200°F. to about 800°F., a pressure of from 500 to about 2,000 psig., a liquid hourly space velocity of about 1.0 to about 10.0 and a hydrogen circulation rate in an amount sufficient to yield a mole ratio of hydrogen to cyclohexane, in the product effluent from the last reaction zone, not substantially less than about 4.0:1. Although not essential, one preferred operating technique involves the use of three reaction zones, each of which contains approximately one-third of the total quantity of catalyst employed. The process is further facilitated when the total fresh benzene is added in three approximately equal portions, one each to the inlet of each of the three reaction zones.

The catalyst utilized is a substantially halogen-free alumina carrier material combined with about 0.50% by weight of germanium, 0.375% by weight of iridium, 0.375% by weight of platinum, and about 0.90% by weight of lithium, all of which are calculated on the basis of the elemental metals. The hydrogenation process will be described in connected with a commercially-scaled unit having a total fresh benzene feed capacity of about 1,488 barrels per day. Make-up gas in an amount of about 741.6 mols/hr. is admixed with 2,396 Bbl./day (about 329 mols/hr.) of a cyclohexane recycle stream, the mixture being at a temperature of about 137°F., and further mixed with 96.24 mols/hr. (582 Bbl./day) of the benzene feed; the final mixture constitutes the total charge to the first reaction zone.

Following suitable heat-exchange with various hot effluent streams, the total feed to the first reaction zone is at a temperature of 385°F. and a pressure of 460 psig. The reaction zone effluent is at a temperature of 606°F. and a pressure of about 450 psig. The total effluent from the first reaction zone is utilized as a heat-exchange medium, in a stream generator, whereby the temperature is reduced to a level of about 545°F. The cooled effluent is admixed with about 98.5 moles per hour (596 Bbl./day) of fresh benzene feed, at a temperature of 100°F.; the resulting temperature is 400°F., and the mixture enters the second reaction zone at a pressure of about 440 psig. The second reaction zone effluent, at a pressure of 425 psig. and a temperature of 611°F., is admixed with 51.21 mols/hr. (310 Bbl./day) of fresh benzene feed, the resulting mixture being at a temperature of 578°F. Following its use as a heat-exchange medium, the temperature is reduced to 400°F., and the mixture enters the third reaction zone at a pressure of 415 psig. The third reaction zone effluent is at a temperature of about 500°F. and a pressure of about 400 psig. Through utilization as a heat-exchange medium, the temperature is reduced to a level of about 244°F., and subsequently reduced to a level of about 115°F. by use of an air-cooled condenser. The cooled third reaction zone effluent is introduced into a high pressure separator, at a pressure of about 370 psig.

A hydrogen-rich vaporous phase is withdrawn from the high pressure separator and recycled by way of compressive means, at a pressure of about 475 psig., to the inlet of the first reaction zone. A portion of the normally liquid phase is recycled to the first reaction zone as the cyclohexane concentrate hereinbefore described. The remainder of the normally liquid phase is passed into a stabilizing column functioning at an operating pressure of about 250 psig., a top temperature of about 160°F. and a bottom temperature of about 430°F. The cyclohexane product is withdrawn from the stabilizer as a bottoms stream, the overhead stream being vented to fuel. The cyclohexane concentrate is recovered in an amount of about 245.80 moles per hour, of which only about 0.60 moles per hour constitutes other hexanes. In brief summation, the the 19,207 pounds per hour of fresh benzene feed, 20,685 pounds per hour of cyclohexane product is recovered.

EXAMPLE II

Another hydrocarbon hydroprocessing scheme, to which the present invention is applicable, involves the hydrorefining of coke-forming hydrocarbon distillates.

The hydrocarbon distillates are generally sulfurous in nature, and contain mono-olefinic, di-olefinic and aromatic hydrocarbons. Through the utilization of a catalytic composite comprising a germanium component, an iridium component and a platinum or palladium component, increased selectively and stability of operation is obtained; selectivity is most noticeable with respect to the retention of aromatics, and in hydrogenating conjugated di-olefinic and mono-olefinic hydrocarbons. Such charge stocks generally result from diverse conversion processes including the catalytic and/or thermal cracking of petroleum, sometimes referred to as pyrolysis, the destructive distillation of wood or coal, shale oil retorting, etc. The impurities in these distillate fractions must necessarily be removed before the distillates are suitable for their intended use, or which when removed, enhance the value of the distillate fraction for further processing. Frequently, it is intended that these charge stocks be substantially desulfurized, saturated to the extent necessary to remove the conjugated di-olefins, while simultaneously retaining the aromatic hydrocarbons. When subjected to hydrorefining for the purpose of removing the contaminating influences, there is encountered difficulty in effecting the desired degree of reaction due to the formation of coke and other carbonaceous material.

As utilized herein, "hydrogenating" is intended to be synonymous with "hydrorefining". The purpose is to provide a highly selective and stable process for hydrogenating coke-forming hydrocarbon distillates, and this is accomplished through the use of a fixed-bed catalytic reaction system utilizing a catalyst comprising a germanium component, an iridium component and a platinum or palladium component. There exists two separate, desirable routes for the treatment of coke-forming distillates, for example a pyrolysis naphtha byproduct. One such route is directed toward a product suitable for use in certain gasoline blending. With this as the desired object, the process can be effected in a single stage, or reaction zone, with the catalytic composite hereinafter specifically described as the first-stage catalyst. The attainable selectivity of this instance resides primarily in the hydrogenation of highly reactive double bonds. In the case of conjugated di-olefins, the selectivity afforded restricts the hydrogenation to produce mono-olefins, and, with respect to the styrenes, for example, the hydrogenation is inhibited to produce alkyl benzenes without "ring" saturation. The selectivity is accomplished with a minimum of polymer formation either to "gums", or lower molecular weight polymers which would necessitate a re-running of the product before blending to gasoline would be feasible. Other advantages of restricting the hydrogenating of the conjugated di-olefins, such as 1,5 normal hexadiene are not unusually offensive in suitably inhibited gasolines in some locales, and will not react in this first stage. Some fresh charge stocks are sufficiently low in mercaptan sulfur content that direct gasoline blending may be considered, although a mild treatment for mercaptan sulfur removal might be necessary. These considerations are generally applicable to foreign markets, particularly European, where olefinic and sulfur-containing gasolines are not too objectionable. It must be noted that the sulfurous compounds, and the mono-olefins, whether virgin, or products of di-olefin partial saturation, are unchanged in the single, or first-stage reaction zone. Where however the desired end result is aromatic hydrocarbon retention, intended for subsequent extraction, the two-stage route is required. The mono-olefins must be substantially saturated in the second stage to facilitate aromatic extraction by way of currently utilized methods. Thus, the desired necessary hydrogenation involves saturation of the mono-olefins, as well as sulfur removal, the latter required for an acceptable ultimate aromatic product. Attendant upon this is the necessity to avoid even partial saturation of aromatic nuclei.

With respect to one catalytic composite, its principal function involves the selective hydrogenation of conjugated di-olefinic hydrocarbons to mono-olefinic hydrocarbons. The particular catalytic composite possesses unusual stability notwithstanding the presence of relatively large quantities of sulfurous compounds in the fresh charge stock. The catalytic composite comprises an alumina-containing refractory inorganic oxide, a germanium component, an iridium component, a platinum or palladium component and an alkali-metal component, the latter being preferably potassium and/or lithium. It is especially preferred, for use in this particular hydrocarbon hydroprocessing scheme, that the catalytic composite be substantially free from any "acid-acting" propensities. The catalytic composite, utilized in the second reaction zone for the primary purpose of effecting the destructive conversion of sulfurous compounds into hydrogen sulfide and hydrocarbons, is a composite of an alumina-containing refractory inorganic oxide, a platinum or palladium component, an iridium component, and a germanium component. Through the utilization of a particular sequence of processing steps, and the use of the foregoing described catalyst composites, the formation of high molecular weight polymers and co-polymers is inhibited to a degree which permits processing for an extended period of time. Briefly, this is accomplished by initiating the hydrorefining reactions at temperatures below about 500°F., at which temperatures the coke-forming reactions are not promoted. The operating conditions within the second reaction zone are such that the sulfurous compounds are removed without incurring the detrimental polymerization reactions otherwise resulting were it not for the saturation of the conjugated di-olefinic hydrocarbons with the first reaction zone.

The hydrocarbon distillate charge stock, for example a light naphtha by-product from a commercial cracking unit designed and operated for the production of ethylene, having a gravity of about 34.0° API, a bromine number of about 35.0, a diene value of about 17.5 and containing about 1,600 ppm. by weight of sulfur and 75.9 vol.% aromatic hydrocarbons, is admixed with recycled hydrogen. This light naphtha co-product has an initial boiling point of about 164°F. and an end boiling point of about 333°F. The hydrogen circulation rate is within the range of from about 1,000 to about 10,000 scf./Bbl., and preferably in the narrower range of from 1,500 to about 6,000 scf./Bbl. The charge stock is heated to a temperature such that the maximum catalyst temperature is in the range of from about 200°F. to about 500°F., by way of heat-exchange with various product effluent streams, and is introduced into the first reaction zone at an LHSV in the range of about 0.5 to about 10.0. The reaction zone is maintained at a pressure of from 400 to about 1,000 psig., and preferably at a level in the range of from 500 psig. to about 900 psig.

The temperature of the product effluent from the first reaction zone is increased to a level above about 500°F., and preferably to result in a maximum catalyst temperature in the range of 600°F. to 900°F. When the process is functioning efficiently, the diene value of the liquid charge entering the second catalytic reaction zone is less than about 1.0 and often less than about 0.3. The coversion of nitrogenous and sulfurous compounds, and the saturation of mono-olefins, contained within the first zone effluent, is effected in the second zone. The second catalytic reaction zone is maintained under an imposed pressure of from about 400 to about 1,000 psig., and preferably at a level of from about 500 to about 900 psig. The two-stage process is facilitated when the focal point for pressure control is the high pressure separator serving to separate the product effluent from the second catalytic reaction zone. It will, therefore, be maintained at a pressure slightly less than the first catalytic reaction zone, as a result of fluid flow through the system. The LHSV through the second reaction zone is about 0.5 to about 10.0, based upon fresh feed only. The hydrogen circulation rate will be in a range of from 1,000 to about 10,000 scf./Bbl., and preferably from about 1,000 to about 8,000 scf./Bbl. Series-flow through the entire system is facilitated when the recycle hydrogen is admixed with the fresh hydrocarbon charge stock. Make-up hydrogen, to supplant that consumed in the overall process, may be introduced from any suitable external source, but is preferably introduced into the system by way of the effluent line from the first catalytic reaction zone to the second catalytic reaction zone.

With respect to the naphtha boiling range portion of the product effluent, the sulfur concentration is about 0.1 ppm., the aromatic concentration is about 75.1% by volume, the bromine number is less than about 0.3 and the diene value is essential "nil".

With charge stocks having exceedingly high diene values, a recycle diluent is employed in order to prevent an excessive temperature rise in the reaction system. Where so utilized, the source of the diluent is preferably a portion of the normally liquid product effluent from the second catalytic reaction zone. The precise quantity of recycle material varies from feed stock to feed stock; however, the rate at any given time is controlled by monitoring the diene value of the combined liquid feed to the first reaction zone. As the diene value exceeds a level of about 25.0, the quantity of recycle is increased, thereby increasing the combined liquid feed ratio; when the diene value approaches a level of about 20.0, or less, the quantity of recycle diluent may be lessened, thereby decreasing the combined liquid feed ratio.

With another so-called pyrolysis gasoline, having a gravity of about 36.4° API, containing 600 ppm. by weight of sulfur, 78.5% by volume of aromatics, and having a bromine number of 45 and a diene value of 25.5 it is initially processed in a first reaction zone containing a catalytic composite of alumina, 0.5% by weight of lithium, 0.20% by weight of palladium, 0.375% by weight of iridium and 0.375% by weight of germanium, calculated as the elements. The fresh feed charge rate is 3,300 Bbl./day, and this is admixed with 2,475 Bbl./day of the normally liquid diluent. Based upon fresh feed only, the LHSV is 2.5 and the hydrogen circulation rate is 1,750 scf./Bbl. The charge is raised to a temperature of about 250°F., and enters the first reaction zone at a pressure of about 840 psig. The product effluent emanates from the first reaction zone at a pressure of about 830 psig. and a temperature of about 350°F. The effluent is admixed with about 660 scf./Bbl. of make-up hydrogen, and the temperature is increased to a level of about 545°F., the heated stream is introduced into the second reaction zone under a pressure of about 790 psig. The LHSV, exclusive of the recycle diluent, is 2.5, and the hydrogen circulation rate is about 1,500. The second reaction zone contains a catalyst of a composite of alumina, 0.375% by weight of platinum, 0.375% by weight of iridium and 0.25% by weight of germanium. The reaction product effluent is introduced following its use as a heat-exchange medium and further cooling, to reduce its temperature from 620°F. to a level of 100°F., into a high-pressure separator at a pressure of about 750 psig. The normally liquid stream from the cold separator is introduced into a reboiled stripping column for hydrogen sulfide removal and depentanization. The hydrogen sulfide stripping column functions at conditions of temperature and pressure required to concentrate a $C_6$ to $C_9$ aromatic stream as a bottoms fraction. With respect to the overall product distribution, only 690 lbs./hr. of pentanes and lighter hydrocarbons is indicated in the stripper overhead. The aromatic concentrate is recovered in an amount of about 40,070 lbs./hr. (the fresh feed is 40,120 lbs./hr); these results are achieved with a hydrogen consumption of only 660 scf./Bbl. With respect to the desired product, the aromatic concentration is 78.0, the sulfur concentration is less than 1.0 ppm. by weight, and the diene value is essentially nil.

EXAMPLE III

This example is presented to illustrate still another hydrocarbon hydroprocessing scheme for the improvement of the jet fuel characteristics of sulfurous kerosene boiling range fractions. The improvement is especially noticeable in the IPT Smoke Point, the concentration of aromatic hydrocarbons and the concentration of sulfur. A two-stage process wherein desulfurization is effected in the first reaction zone at relatively mild severities which result in a normally liquid product effluent containing from about 15 to about 35 ppm. of sulfur by weight. Aromatic saturation is the principal reaction effected in the second reaction zone, having disposed therein a catalytic composite of alumina, a halogen component, a platinum or palladium component, an iridium component and a germanium component.

Suitable charge stocks are kerosene fractions having an initial boiling point as low as about 300°F., and an end boiling point as high as about 575°F., and, in some instances, up to 600°F. Examplary of such kerosene fractions are those boiling from about 300°F. to about 550°F., from 330°F. to about 500°F., from 330°F. to about 530°F., etc. As a specific example, a kerosene obtained from hydrocracking a Mid-continent slurry oil, having a gravity of about 30.5° API, an initial boiling point of about 388°F., an end boiling point of about 522°F., has an IPT Smoke Point of 17.1 mm., and contains 530 ppm. of sulfur and 24.8% by volume of aromatic hydrocarbons. Through the use of the catalytic process of the present invention, the improvement in the jet fuel quality of such a kerosene fraction is most significant with respect to raising the IPT Smoke Point, and reducing the concentration of sulfur and the quantity of aromatic hydrocarbons. Specifications regarding the poorest quality of jet fuel, commonly referred to as Jet-A, Jet-A1 and Jet-B call for a sulfur concentration of about 0.3% by weight maximum (3,000 ppm.), a minimum IPT Smoke Point of 25 mm. and a maximum aromatic concentration of about 20.0 vol. %.

The charge stock is admixed with circulating hydrogen in an amount within the range of from about 1,000 to about 2,000 scf./Bbl. This mixture is heated to a temperature level necessary to control the maximum catalyst bed temperature below about 750°F., and preferably not above 700°F., with a lower catalyst bed temperature of about 600°F. The catalyst, a well known standard desulfurization catalyst containing about 2.2% by weight of cobalt and about 5.7% by weight of molybdenum, composited with alumina is disposed in a reaction zone maintained under an imposed pressure in the range of from about 500 to about 1,000 psig. The LHSV is in the range of about 0.5 to about 10.0, and preferably from about 0.5 to about 5.0. The total product effluent from this first catalytic reaction zone is separated to provide a hydrogen-rich gaseous phase and a normally liquid hydrocarbon stream containing 15 ppm. to about 35 ppm. of sulfur by weight. The normally liquid phase portion of the first reaction zone effluent is utilized as the fresh feed charge stock to the second reaction zone. In this particular instance, the first reaction zone decreases the sulfur concentration to about 25 ppm., the aromatic concentration to about 16.3% by volume, and has increased the IPT Smoke Point to a level of about 21.5 mm.

The catalytic composite within the second reaction zone comprises alumina, 0.375% by weight of platinum, 0.375% by weight of iridium, 0.30% by weight of germanium and about 0.60% by weight of combined chloride, calculated on the basis of the elements. The reaction zone is maintained at a pressure of about 400 to about 1,500 psig., and the hydrogen circulation rate is in the range of 1,500 to about 10,000 scf./Bbl. The LHSV, hereinbefore defined, is in the range of from about 0.5 to about 5.0, and preferably from about 0.5 to about 3.0. It is preferred to limit the catalyst bed temperature in the second reaction zone to a maximum level of about 750°F. With a catalyst of this particular chemical and physical characteristics, optimum aromatic saturation, processing a feed stock containing from about 15 to about 35 ppm. of sulfur, is effected at maximum catalyst bed temperatures in the range of about 625°F. to about 750°F. With respect to the normally liquid kerosene fraction, recovered from the condensed liquid removed from the total product effluent, the sulfur concentration is effectively nil, being about 0.1 ppm. The quantity of aromatic hydrocarbons has been decreased to a level of about 0.75% by volume, and the IPT Smoke Point has been increased to about 36.3 mm.

With respect to another kerosene fraction, having an IPT Smoke Point of about 20.5 mm., an aromatic concentration of about 19.3 vol.% and a sulfur concentration of about 17 ppm. by weight, the same is processed in a catalytic reaction zone at a pressure of about 850 psig. and a maximum catalyst bed temperature of about 725°F. The LHSV is about 1.35, and the hydrogen circulation rate is about 8,000 scf./Bbl. The catalytic composite disposed within the reaction zone comprises alumina, 0.25% by weight of platinum, 0.25% by weight of iridium, 0.40% by weight of germanium, about 0.35% by weight of combined chloride and 0.35% by weight of combined fluoride. Following separation and distillation, to concentrate the kerosene fraction, analyses indicate that the Smoke Point has been increased to a level of about 36.9 mm., the aromatic concentration has been lowered to about 0.6% by volume and the sulfur concentration is essentially nil.

EXAMPLE IV

This illustration of a hydrocarbon hydroprocessing scheme, encompassed by my invention is one which involves hydrocracking heavy hydrocarbonaceous material into lower-boiling hydrocarbon products. In this instance, the preferred catalysts contain a germanium component, a platinum or palladium component, an iridium component, combined with a crystalline aluminosilicate-carrier material, preferably faujasite, and still more preferably one which is at least 90.0% by weight zeolitic.

Most of the virgin stocks, intended for hydrocracking, are contaminated by sulfurous compounds and nitrogenous compounds, and, in the case of the heavier charge stocks, various metallic contaminants, insoluble asphalts, etc. Contaminated charge stocks are generally hydrorefined in order to prepare a charge suitable for hydrocracking. Thus, the catalytic process of the present invention can be beneficially utilized as the second stage of a two-stage process, in the first stage of which the fresh feed is hydrorefined.

Hydrocracking reactions are generally effected at elevated pressures in the range of about 800 to about 5,000 psig., and preferably at some intermediate level of 1,000 to about 3,500 psig. Liquid hourly space velocities of about 0.25 to about 10.0 will be suitable, the lower range generally reserved for the heavier stocks. The hydrogen circulation rate will be at least about 3,000 scf./Bbl., with an upper limit of about 50,000 scf./Bbl., based upon fresh feed. For the majority of feed stocks, hydrogen circulation in the range of 5,000 to 20,000 scf./Bbl. will suffice. With respect to the LHSV, it is based upon fresh feed, notwithstanding the use of recycle liquid providing a combined liquid feed ratio in the range of about 1.25 to about 6.0. The operating temperature again alludes to the temperature of the catalyst within the reaction zone, and is in the range of about 400°F. to about 900°F. Since the principal reactions are exothermic in nature, the increasing temperature gradient, experienced as the charge stock traverses the catalyst bed, results in an outlet temperature higher than that at the inlet to the catalyst bed. The maximum catalyst temperature should not exceed 900°F., and it is generally a preferred technique to limit the temperature increase to 100°F. or less.

Although amorphous composites of alumina and silica, containing from about 10.0% to about 90.0% by weight of the latter, are suitable for use in the catalytic composite employed in the present process, a preferred carrier material constitutes a crystalline aluminosilicate, preferably faujasite, of which at least about 90.0% by weight is zeolitic. This carrier material, and a method of preparing the same, have hereinbefore been described. Generally, the germanium component will be used in an amount sufficient to result in a final catalytic composite containing about 0.01% to about 5.0% by weight. The iridium component will be used in an amount sufficient to result in a final catalytic composite containing about 0.01% to about 2% by weight. The platinum or palladium component is generally present in an amount within the range of about 0.01% to about 2.0% by weight, and may exist within the composite as a compound such as an oxide, sulfide, halide, etc. Another possible constituent of the catalyst is a halogen component, either fluorine, chlorine, iodine, bromine, or mixtures thereof. Of these, it is preferred to utilize a catalyst containing fluorine and/or chlorine. The halogen component will be composited with the carrier material in such a manner as results in a final composite containing about 0.1% to about 1.5% by weight of halogen, calculated on an elemental basis.

A specific illustration of this hydrocarbon hydroprocessing technique involves the use of a catalytic composite of about 0.4% by weight of platinum, 0.375% by weight of iridium 0.7% by weight of combined chlorine, and 0.4% by weight of germanium, combined with a crystalline aluminosilicate material of which about 90.9% by weight constitutes faujasite. This catalyst is intended for utilization in the conversion of 16,000 Bbl./day of a blend of light gas oils to produce maximum quantities of a heptane-400°F. gasoline boiling range fraction. The charge stock has a gravity of 33.8° API, contains 0.19% by weight of sulfur (1,900 ppm.) and 67 ppm. by weight of nitrogen, and has an initial boiling point of 369°F., a 50% volumetric distillation temperature of 494°F. and an end boiling point of 655°F. The charge stock is initially subjected to a clean-up operation at maximum catalyst temperature of 750°F., a combined feed ratio of 1.0 an LHSV of 2.41 with a hydrogen circulation rate of about 5000 scf./Bbl. The pressure imposed upon the catalyst within the reaction zone is about 1,500 psig. Since at least a portion of the blended gas oil charge stock will be converted into lower-boiling hydrocarbon products, the effluent from this clean-up reaction zone is separated to provide a normally liquid, 400°F.-plus charge for the hydrocracking reaction zone containing the platinum-iridium-germanium-chloride catalyst. The pressure imposed upon the second reaction zone is about 1,500 psig., and the hydrogen circulation rate is about 8,000 scf./Bbl. The original quantity of fresh feed to the clean-up reaction zone is about 16,000 Bbl./day; following separation of the first zone effluent to provide the 400°F.-plus charge to the second reaction zone, the charge to the second reaction zone is in an amount of about 12,150 Bbl./day, providing an LHSV of 0.85. The temperature at the inlet to the catalyst bed is 665°F., and a conventional hydrogen quench stream is utilized to maintain the maximum reactor outlet temperature at about 700°F. Following separation of the product effluent from the second reaction zone, to concentrate the desired gasoline boiling range fraction, the remaining 400°F.-plus normally liquid material, in an amount of 7,290 Bbl./day, is recycled to the inlet of the second reaction zone, thus providing a combined liquid feed ratio thereto of about 1.60. In the following table, there is indicated the product yield and distribution of this process. With respect to normally liquid hydrocarbons, for convenience including butanes; the yields are given in vol. %; with respect to the normally gaseous hydrocarbons, ammonia and hydrogen sulfide, the yields are given in terms of wt. %. With respect to the first reaction zone, the hydrogen consumption is 1.31% by weight of the fresh feed (741 scf./Bbl.), and for the hydrocracking reaction zone, 1.26% by weight of the fresh feed charge stock, or 713 scf./Bbl.

TABLE

| Hydrocracking Product Yield and Distribution | | | |
| --- | --- | --- | --- |
| Component | Stage I | Stage II | Total |
| Ammonia | 0.01 | — | 0.01 |
| Hydrogen Sulfide | 0.21 | — | 0.21 |
| Methane | 0.12 | 0.02 | 0.14 |
| Ethane | 0.22 | 0.40 | 0.62 |
| Propane | 1.03 | 3.48 | 4.51 |
| Butanes | 3.90 | 14.66 | 18.56 |
| Pentanes | 3.04 | 11.28 | 14.32 |
| Hexanes | 3.00 | 11.21 | 14.21 |
| C$_7$-400°F. | 18.85 | 49.56 | 68.41 |
| 400°F.-plus | 75.92* | — | — |

*Charge to Stage II

With respect to both the butane product and pentane product, the former is indicated as being about 680% isobutanes, while the latter constitutes about 930% iospentanes. An analysis of the combined pentane/hexane fraction indicates a gravity of 82.6° API, a clear research octane rating of 85.0 and a leaded research octane rating of 99.0; it will be noted that this constitutes an excellent blending component for motor fuel. The desired heptane-400°F. product indicates a gravity of 48.8° API, a clear research octane rating of 72.0 and a leaded research octane rating of 88.0. This gasoline boiling range fraction constitutes about 34.0% by volume paraffins, 36.0% by volume naphthenes and 30.0% by volume aromatic hydrocarbons. It will be recognized that this gasoline boiling range fraction constitutes an excellent charge stock for a catalytic reforming unit to improve the motor fuel characteristics thereof.

The foregoing specification, and particularly the examples, indicates the method by which the present invention is effected, and the benefits afforded through the utilization thereof.

I claim as my invention:

1. A hydrocarbon hydroprocess for hydrogenating a coke-forming hydrocarbon distillate containing di-olefinic and mono-olefinic hydrocarbons and aromatics which process comprises reacting said distillate with hydrogen at a temperature below about 500°F. and at conditions selected to effect chemical consumption of hydrogen, in contact with a catalytic composite of a platinum or palladium component, an iridium component, a germanium component and a porous carrier material, substantially all of the platinum or palladium component and the iridium component being in the elemental metallic state and the germanium component being in an oxidation state above that of the elemental metal and recovering an aromatic/mono-olefinic hydrocarbon concentrate substantially free from conjugated di-olefinic hydrocarbons.

2. The process of claim 1 further characterized in that said catalytic composite comprises from about 1% to about 5% by weight of an alkalinous metal component.

3. The process of claim 1 further characterized in that said conditions include a pressure from about 400 to about 5000 psig., a liquid hourly space velocity from about 0.1 to about 10, and a hydrogen circulation rate from about 1,000 to about 50,000 scf./Bbl.

4. The process of claim 1 further characterized in that said catalytic composite contains from about 0.01% to about 2% by weight of said platinum or palladium component, from about 0.01% to about 2% by weight of said iridium component and from about 0.01% to about 5% by weight of said germanium component, calculated on an elemental basis.

* * * * *